United States Patent
Lindberg et al.

(10) Patent No.: US 8,750,959 B2
(45) Date of Patent: *Jun. 10, 2014

(54) WEARING APPAREL WITH A SENSOR FOR MEASURING A PHYSIOLOGICAL SIGNAL

(75) Inventors: Phillip Lindberg, Helsinki (FI); Kimmo Pernu, Espoo (FI); Jukka Manni, Helsinki (FI); Jorma Liljemark, Järvenpää (FI); Tapio Savolainen, Helsinki (FI); Hannu Putkinen, Helsinki (FI); Jari Akkila, Helsinki (FI); Satu Rahkonen, Espoo (FI); Erik Lindman, Espoo (FI)

(73) Assignee: Suunto Oy, Vantaa (FI)

( * ) Notice: Subject to any disclaimer, the term of this patent is extended or adjusted under 35 U.S.C. 154(b) by 0 days.

This patent is subject to a terminal disclaimer.

(21) Appl. No.: 13/618,481

(22) Filed: Sep. 14, 2012

(65) Prior Publication Data

US 2013/0123601 A1 May 16, 2013

Related U.S. Application Data

(63) Continuation of application No. 11/808,391, filed on Jun. 8, 2007, now Pat. No. 8,386,009.

(30) Foreign Application Priority Data

Jun. 8, 2006 (FI) ...................................... 20065391

(51) Int. Cl.
*A61B 5/0408* (2006.01)

(52) U.S. Cl.
USPC ............ 600/386; 600/388; 600/390; 600/393

(58) Field of Classification Search
USPC .................................. 600/386, 388–390, 393
See application file for complete search history.

(56) References Cited

U.S. PATENT DOCUMENTS

| | | |
|---|---|---|
| 3,888,240 A | 6/1975 | Reinhold, Jr. et al. |
| 4,082,087 A | 4/1978 | Howson |
| 4,365,634 A | 12/1982 | Bare et al. |
| 4,370,984 A | 2/1983 | Cartmell |
| 4,398,545 A | 8/1983 | Wilson |
| 4,539,995 A | 9/1985 | Segawa |
| 4,669,479 A | 6/1987 | Dunseath, Jr. |
| 4,729,377 A | 3/1988 | Granek et al. |
| 4,763,660 A | 8/1988 | Kroll et al. |

(Continued)

FOREIGN PATENT DOCUMENTS

| | | |
|---|---|---|
| EP | 1752093 A2 | 2/2007 |
| WO | WO 02/071935 A1 | 9/2002 |
| WO | WO 03/082103 A1 | 10/2003 |
| WO | WO 2005/032366 A1 | 4/2005 |

*Primary Examiner* — Lee S Cohen
(74) *Attorney, Agent, or Firm* — Birch, Stewart, Kolach & Birch, LLP (57) ABSTRACT

An article of wearing apparel provided with a sensor for measuring a physiological signal, and a method for manufacturing the wearing apparel provided with a sensor. The wearing apparel includes a flexible substrate and the sensor includes at least one electrode, which has a signalling surface, and which faces in the same direction as the first surface of the flexible substrate. In addition, the sensor includes a signal transmission conductor, which is connected electrically to the electrode. The signal transmission conductor is attached in a watertight manner to the second surface of the substrate. The wearing apparel is comfortable to the user, and sensor in the wearing apparel is reliable, economical to manufacture, and waterproof.

37 Claims, 5 Drawing Sheets

(56) References Cited

U.S. PATENT DOCUMENTS

| | | |
|---|---|---|
| 5,090,410 A | 2/1992 | Saper et al. |
| 5,263,481 A | 11/1993 | Axelgaard |
| 5,511,553 A | 4/1996 | Segalowitz |
| 5,947,897 A | 9/1999 | Otake |
| 6,080,690 A | 6/2000 | Lebby et al. |
| 6,315,719 B1 | 11/2001 | Rode et al. |
| 6,381,482 B1 | 4/2002 | Jayaraman et al. |
| 6,453,186 B1 | 9/2002 | Lovejoy et al. |
| 7,308,294 B2 * | 12/2007 | Hassonjee et al. ............ 600/386 |
| 7,559,902 B2 * | 7/2009 | Ting et al. ..................... 600/529 |
| 8,386,009 B2 * | 2/2013 | Lindberg et al. .............. 600/388 |
| 2002/0082491 A1 | 6/2002 | Nissila |
| 2005/0043641 A1 | 2/2005 | Ueda |
| 2006/0094948 A1* | 5/2006 | Gough et al. ................. 600/372 |
| 2006/0167353 A1 | 7/2006 | Nazeri |
| 2006/0224072 A1 | 10/2006 | Shennib |
| 2006/0234584 A1* | 10/2006 | Valentine ...................... 442/304 |
| 2007/0149887 A1 | 6/2007 | Hwang et al. |

\* cited by examiner

WEARING APPAREL WITH A SENSOR FOR MEASURING A PHYSIOLOGICAL SIGNAL

The present application is a Continuation Application which claims priority under 35 U.S.C. §120 to U.S. patent application Ser. No. 11/808,391 filed Jun. 8, 2007, now U.S. Pat. No. 8,386,009, and to FI 20065391, filed in Finland on Jun. 8, 2006, and on which priority is claimed under 35 U.S.C. §119.

BACKGROUND OF THE INVENTION

1. Field of the Invention

The present invention relates to wearing apparel with sensor devices. In particular the invention relates to wearing apparel with new sensor for measuring a physiological signal from the skin. Such sensor typically comprises a substrate, a signal electrode, and means from transmitting a signal electrically. In addition, the invention relates to a method for manufacturing wearing apparel with a sensor, such as a heart rate belt or sports brassiere.

2. Description of Background Art

Traditional heart-rate meter heart rate bands and heart rate belts generally comprise a body made of plastic, on the surface of which there are two local electrodes to be placed against the chest. Electronics for transmitting a heart rate signal, typically to a wristop device, are built into the plastic body. Conductors from the electrodes to the electronics also run inside the body, which is generally attached against the chest with the aid of a flexible band.

Because plastic heart rate bands are relatively thick and can feel uncomfortable in use, heart rate belts and sensor utilizing textile materials in particular have been developed recently. One such is disclosed in WO publication 2005/032366. In the solution depicted in it, the electrodes and transmission conductors are surfaced with a conductive material directly in the textile material. The transmission conductors can afterwards be coated with an insulating material, so that only the electrodes remain in contact with the skin and the quality of the signal improves. However, the laminate then remains on the surface of the product at the conductors, so that the breathability of these locations is reduced and they may feel uncomfortable against the skin.

WO publication 2002/071935 (FI 110915) discloses a heart rate sensor, in which there are electrodes containing conductive fibres, at the ends of which there is a moisture-retaining layer to improve the electrical contact of the electrodes with the skin. This solution also has a problem with the placing of the signal transmission conductors relative to the fibre material, particularly with creating both reliable contacts with the electrodes for them and good electrical insulation.

WO publication 2003/082103 discloses a heart rate sensor, with electrodes made by moulding through a textile material. The electrical conductors can be added to the mould, in order to attach them securely to the electrode moulding. However, the electrical conductors remain loose of the surface of the fabric and liable to mechanical stresses acting on them. They can also be attached as part of the textile with the aid of thermo-compression, but then a powerful interference signal may connect to them from the skin through the fabric.

US publication 2005/0043641 discloses a device intended to measure heart rate, which can be detachably attached to a flexible band, or piece of apparel, with the aid of hooks in it. Though it can be attached to many different pieces of apparel, it does not eliminate the problem of discomfort when using traditional heart rate bands.

SUMMARY AND OBJECTS OF THE INVENTION

The invention is intended to eliminate the defects of the state of the art disclosed above, and for this purpose, to create an article of wearing apparel provided with a flexible sensor on a textile substrate of the wearing article, which is easily manufactured.

In the sensor according to the invention for measuring a physiological signal, the outer layer is a flexible and moisture-permeable substrate, which has an outer surface (first surface) and an inner surface (second surface) opposite to this. A signal transmission conductor is arranged in a watertight manner on the inner surface of the substrate, so that interference signals cannot connect directly from the skin through the substrate. An electrode, with a signalling surface facing in the same direction as the outer surface of the flexible substrate, is in turn connected electrically to the transmission conductor.

In the method according to the invention for manufacturing the wearing apparel having a sensor, a flexible substrate is taken, which has an inner surface and an outer surface opposite to this. A signal transmission conductor, which is electrically connected to the electrode, is attached to the second surface of the substrate. The electrode is positioned relative to the substrate in such a way that its signalling surface faces in the same direction as the outer surface of the substrate.

The substrate is preferably a textile material or some other fibre manufacture. The electrode can be made of, for example, metal, or a conductive plastic, elastomer, individual fibres, or of a fibre material, such as a woven or knitted fabric. The transmission conductor can be of metal, a conductive plastic, a conductive rubber, a conductive elastomer, a conductive ink, a conductive polymer, a coating with a metal-particle content, a conductive fibre, a pack of fibres, or a fibre manufacture such as a conductive fabric.

The sensor typically comprises a construction of at least three layers, in which there is a substrate layer that remains against the skin, a first insulating layer, and a conductor layer. Further, yet another insulating layer is typically arranged on the second surface of the conductor layer as a fourth layer. The task of the insulating layer is to prevent liquid, for example, perspiration that accumulates in the substrate during exercise, from reaching the conductor layer and thus to prevent an electrical contact arising with the signal conductor and undesirable interference connecting with the electrode signal.

Considerable advantages are gained with the aid of the invention. In the construction according to it, it is possible to combine flexibility of the structure and reliability of the signalling with the sensor's comfort in use. In particular, it permits the use of durable textiles substrates of a tested comfort, directly against the skin either entirely or nearly entirely in the whole area of the sensor. The transmission conductor of the signal is protected against stress, moisture, and electrical interference on the second side of the textile.

The construction according to the invention can also be manufactured entirely form the inner surface of the substrate, in which case the outer surface coming against the user remains untouched, except for the electrode openings. Thus, for example, the comfort and breathability of the textile substrate remain good, even at the conductors. The conductors also remain behind the textile layer, well protected from mechanical stress.

With the aid of the invention, the construction of a sensor product can also be implemented in such a way that the conductor structure remains in such a position in the finished sensor product that no elongating forces act on it when the product bends, or at least such forces are considerably smaller in the outer layers of the product. Thus such unstretchable and poorly stretchable conductor materials too can be used, which has been impossible in earlier solutions.

In particular, such a construction, in which the substrate, the first insulating layer, the conductor/electrode layer, and the second insulating are joined together as a pack, is advantageous in terms of manufacturing technique and use. If the insulating layers are attached to each other at the edges, a conductor structure will be achieved, which is insulated from moisture travelling both parallel to the surface and at right angles to the surface, and which is, in addition, thin and flexible. Such a structure can implemented in both a heart rate belt and in apparel.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings, which are given by way of illustration only, and thus are not limitative of the present invention, and wherein.

DETAILED DESCRIPTION OF THE PREFERRED EMBODIMENTS

Figure 1:
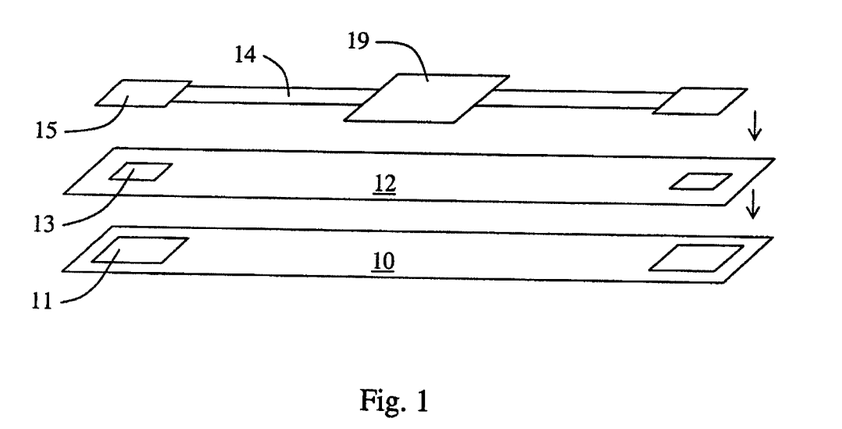
FIGS. 1-3 show exploded views of constructions according to preferred embodiments of the invention.

In FIG. 1, the substrate is marked with the reference number 10. An opening 11 is made in it for an electrode contact. A moisture-insulating intermediate layer 12 is attached permanently on top of the substrate. An opening 13, which can essentially coincide with the opening 11 can also be made in the intermediate layer. The openings 11 and 13 can, of course, also be made later in a single work stage. The electrode 15 is positioned relative to the opening 11 in the substrate and to the opening 13 in the intermediate layer, so that there is a contact connection to its signalling surface from the outer surface of the substrate 10 (from the skin). The signal transmission conductor 14 is attached on top of the intermediate layer 12. Thus the signal transmission conductor 14 is attached to the substrate 10 with the aid of the electrically insulating and watertight layer 12, which is located between the strip-like signal transmission conductor 14 and the substrate 10. At one end, the conductor is connected electrically to the electrode 15. At the other, its other end it is connected to the electronics module, or to the module's installation means 19.

The substrate can be, for example, of a textile material manufactured from natural fibres and/or artificial fibres. The material can be woven or non-woven. It is preferably self-breathing, i.e. permeable by air and water vapour, and often also water. Thus is creates a comfortable feeling against the user's skin.

Figure 2A:
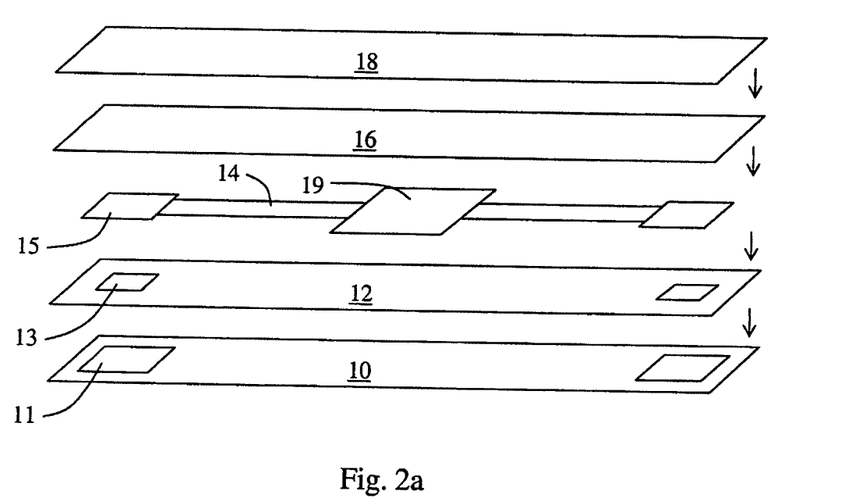

In FIG. 2a, the construction is further extended by adding a second intermediate layer 16 and surface layer 18. The layer 16 ensures that the signal transmission conductor 14 will be watertight also from the second side. The layers 12 and 16 are attached directly to each other at the sides, so that the signal transmission conductor layer 14 remains watertight between them.

According to one embodiment, the substrate continues unbroken from the sensor side facing against the skin to the side opposite to the sensor. Thus the substrate can surround the pack formed of the signal transmission conductor and the intermediate layer or intermediate layers from all sides, in which case both surfaces of the sensor will be formed of an unbroken material. Applied to the embodiment of FIG. 2a (and of FIG. 2b, to be examined in greater detail hereinafter), the substrate 10 and surface layer 18 thus consist of the same unified material, which is bent at the sides of the sensor, in such a way that it encloses the other layer inside it. It is possible to use, for example, a sensor surface element arranged in a tubular form, inside which the other layers of the sensor are placed. The other layers can be laminated as a ready pack before being placed inside the tubular surface layer. Alternatively, a planar substrate layer can be bent over the layers to the other side of the sensor after the application of the other layers and a joint can be formed on this side, for example, with the aid of adhesive. Opening for the electrodes 15 and the electronics module connection are made in the tubular surface element. With the aid of the embodiments described, a tidy appearance is created in the edges of the sensor and the use of separate surface-layer elements is avoided.

According to one preferred embodiment, the second intermediate layer 16 is electrically insulating. It will then be possible to apply a second conductor structure on top of it. Such a second conductor structure can be used to create a second signal path, or electrical shielding layer. Thus with the aid of such a construction it is also possible to increase the sensoring channels, or electromagnetic interference coming from the direction of the second surface can be effectively eliminated. The intermediate layers 12 and 16 are preferably of the same material. Always depending on the thickness and conductor structures of the intermediate layers, there can be several such layers, with no significant increase in the thickness of the sensor. More conductors can also be manufactured in a single layer and/or they can be overlapped in different layers.

According to one preferred embodiment, a conductor layer shielding from electromagnetic interference is arranged under and/or on top of the signal transmission conductor (transfer path) 14, with the aid of the insulator-conductor layering technique described above. Two shielding layers can further be connected electrically to each other at the edges, in order to form a complete jacket for the signal transmission conductor 14.

According to one embodiment, the intermediate layers 12 and/or 16 include electrically insulating laminates. The necessary conductor layers are applied to the substrate 10 and/or with each other on top of the laminates, before they are layered. Such a manufacturing manner is very easy to implement, cheap, and also retains its flexibility after the application of several layers. The laminate is preferably of a barrier type, generally a thin layer attached with the aid of heat, pressure, heat and pressure, or adhesive. For example, many seam laminates used in the apparel industry are suitable for this purpose. The laminate can at the same time also extend to the environment of the electrode 15, as illustrated in FIGS. 1 and 2a. Thus it reinforces the areas of the substrate 10 in the vicinity of the electrode 15, and possibly even prevents the substrate 10 from fraying around the hole 11 made in it.

According to one embodiment, the signal transmission conductor (transfer path) 14 includes a conductor substance, such as a conductive ink, a conductive polymer, or a coating with a metal-particle content, which can be spread in a fluid form. Such a conductor substance is spread on the support layer, the intermediate layer 12 and/or 16 being preferably used as such. In such a case, a surface of the intermediate layer is preferred wherein it is possible to print directly onto the surface, i.e. the surface is print-ready. According to one aspect of the invention, a new use is indeed offered for a laminate attached to a textile substrate, as a base for a conductor material to be applied in a liquid form.

The signal transmission conductor 14 can also comprise a conductor applied in a solid form, such as a rubber or elastomer conductor, a metal conductor, a conductive fibre, or a conductive textile. In this case too, the conductor 14 is preferably attached to the support structure or intermediate layer described above. Particularly TPU elastomer is well suited to this purpose.

According to one preferred embodiment, the signal-transmission conductor 14 is non-metallic, in which case its conductivity can be in the range of, for example, $10^{-10}$-$10^{-2}$% of the conductivity of a metal (copper). The permanent integration of non-metallic conductors with the layered construction presented is typically simpler than that of a metallic conductor, for example, using processes used in the textile industry.

The electrode 15 and the signal transmission conductor 14 can form a unified structure and/or consist of the same material, particularly if a conductive substance produced in a solid form is used.

An intermediate layer attached to the substrate 10, like the laminate described above, can be arranged to make the sensor non-stretchable or poorly stretchable. In that case too the flexibility of the structure will advantageously remain good. In particular, a non-stretchable intermediate layer will be appropriate, if a poorly stretchable signal conductor is used. By means of the pack construction described, the situation is thus achieved, in which the laminate layer or layers, possibly together with the textile layers, carrying the forces acting on the sensor.

Figure 2B:
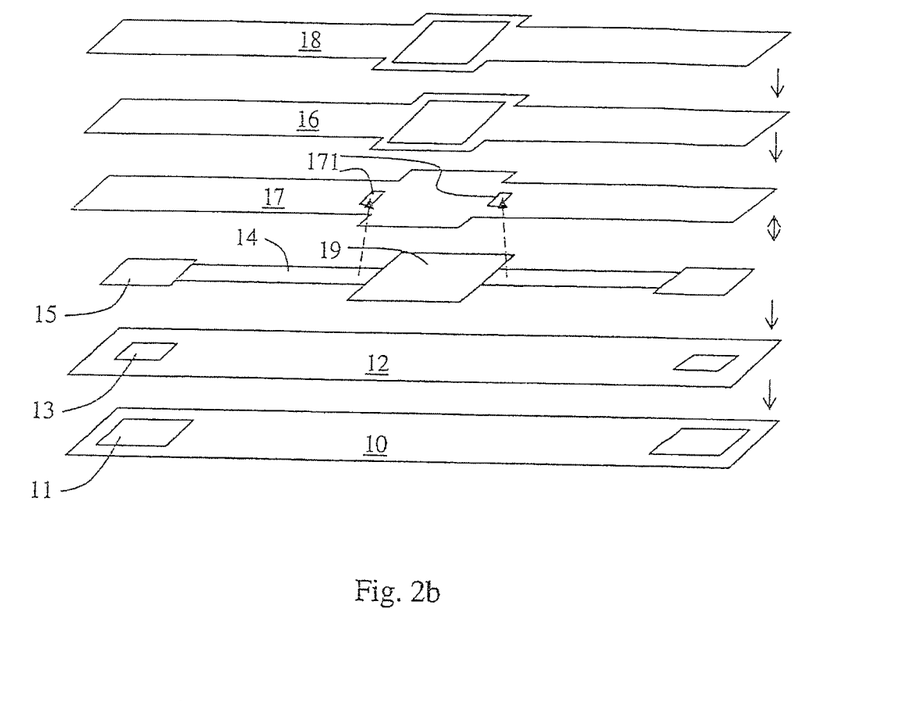
Figure 3:
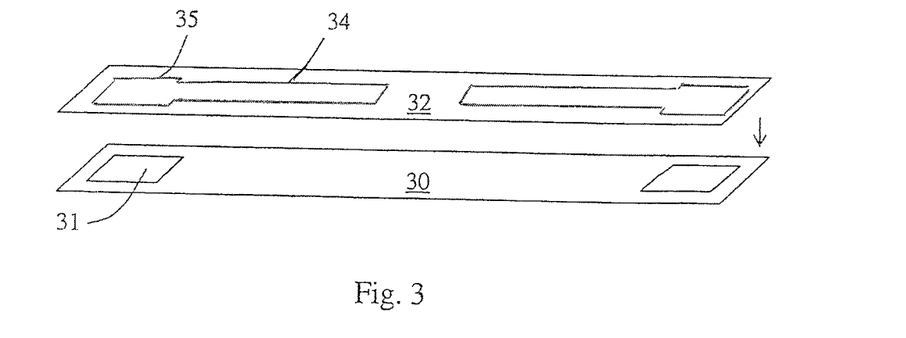

FIG. 2b shows a construction particularly suitable for heart rate belts. In it there is additionally a layer 17, which is arranged on top of the electrodes 15 and the signal transmission conductor 14, but under the electronics module, or its installation zone 19. Thus, it formed a base for the installation zone 19. In the layer 17, there are openings 171, through which the overlapping of the layers can be implemented in such a way that the signal transmission conductor 14 is taken through the opening 171, or a contact between the signal transmission conductor 14 and the installation zone 19 is made at the location of the opening 171. At the same time, the layer 17 can also act as moisture protection for the signal transmission conductor 14, and thus replace the intermediate layer 16 for this purpose. In the construction shown, mainly, for example, the textile-like surface layer 18 of the laminate layer 16 is used to attach the surface layer 18 to the sensor. At the same time, however, it protects and covers the openings 171 and thus protects the contacts from moisture. FIG. 3 shows the sensor of the present invention including a flexible substrate 30, and at least one electrode 35 on intermediate layer 32. The electrode 35 has a signalling surface, which faces in the same direction as the first surface of the flexible substrate 30. In addition, the sensor comprises a signal transmission conductor 34, which is connected electrically to electrode 35. Signal transmission conductor 34 is attached in a watertight manner to the second surface of the substrate 30, with electrode 35 being position directly above opening 31 of substrate 30. The sensor according to the invention is reliable, economical to manufacture, and comfortable to the user.

Figure 4A:
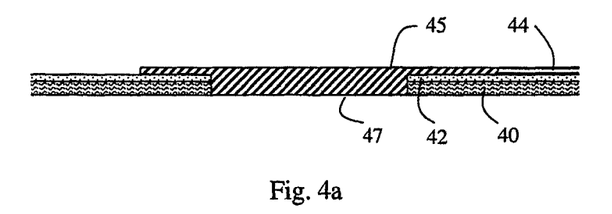
FIGS. 4a-4c show cross-sections of various sensor constructions more closely in the environment of the electrode.
Figure 4B:
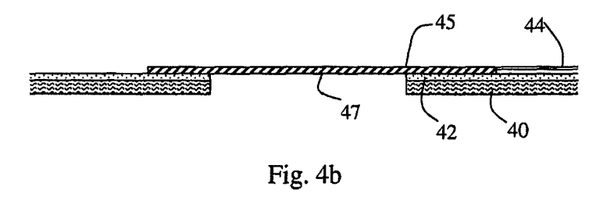
Figure 4C:
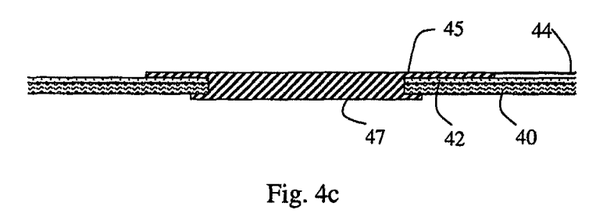

It can be seen from FIGS. 4a-4c that the electrode 45 is arranged on the substrate 40 in such a way that there is a direct contact connection from the side of the first surface of the substrate 40 to the signalling surface 47. The signalling surface 47 is preferably at least on the same level as the first surface of the substrate 40, as in FIGS. 4a and 4c. In some applications, it can also be deeper than the level of the surface of the substrate 40 in the manner shown in FIG. 4b, particularly in the case of very thin substrates and/or when using electrodes with a very large surface area. In the figures, the laminate or other intermediate layer is marked with the reference number 42, and the signal transmission conductor, which is connected to the electrode and directly on top of the laminate 42, is marked with the reference number 44.

An opening for the electrode 45 is preferably made in the substrate 40. The electrode 45 can be arranged at the location of the opening, or through the opening to, or through the surface of the substrate 40, using several different techniques. It can be brought to it as a ready fixed piece, in which case it is generally attached directly to the substrate 40, or to an intermediate layer arranged on top of it, in which there is preferably also an opening. If necessary, it is possible to use adhesives. The electrode 45 can also be vulcanized, or sewn onto the substrate 40. Part of the substrate 40 can also be treated to become conductive, for example, by impregnating it with a conductive substance, or coating the fibres of the substrate 40 with a conductive substance. Suitable conductive substances are conductive polymers, inks, and adhesives. The electrode 45 can also be insulated at the sides, in such a way that it is not in electrical contact with the substrate 40 in these parts, or at all, in which case the signal will connect to the electrodes 45 only through the signalling surface 47, even when the substrate 40 is wet.

Figure 5:
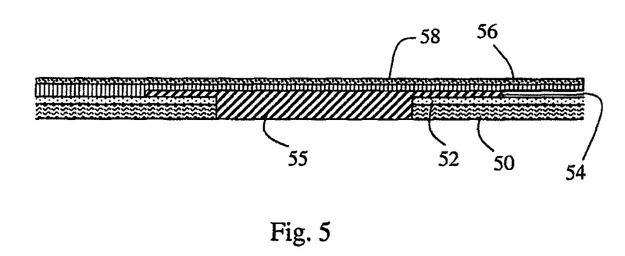
FIG. 5 shows a cross-section of a sensor construction, which is protected from both sides.

With reference to FIG. 5, the sensor structure can, after the application of the electrode 55 and the signal transmission conductor 54, be advantageously extended, in such a way that the signal transmission conductor 54 remains in an inner layer of the sensor structure. This preferably takes place in such a way that the stretch of the transmission conductor 54 when the finished structure is bent is substantially less than that of the outer layers 50, 56 of the structure. Thus, such material layers 50, 52, 56, 58, or layer constructions, with relatively similar elongation and bending properties, are preferable on both sides of the signal transmission conductor layer 54. Their elongations generally differ from each other by 30% at the most and preferably by less than 15%. In that case, the signal transmission conductor 54 will remain essentially on the zero axis of the bending elongation of the structure. Such an embodiment will protect the conductor from unnecessary elongation and contraction when using the sensor, and permit the sensor to be packed in a small space, for example a roll, without damage. The washing of the sensor, especially machine washing, will also stress the signal transmission conductor layer 54 mechanically, if it is wrongly located relative to the layers of the sensor.

The sensor according to the invention is suitable for use particularly in detecting the heart rate of the heart from the skin, for example, from the chest. Thus the sensor also typically comprises a second electrode like that described above and a second corresponding signal conductor to be place on a different side of the chest. The sensor can also be used for measuring other electrical functions or properties of the body. Examples are measurement of the conductivity of the skin and of fat percentages, as well as the detection of muscle activation.

Figure 8:
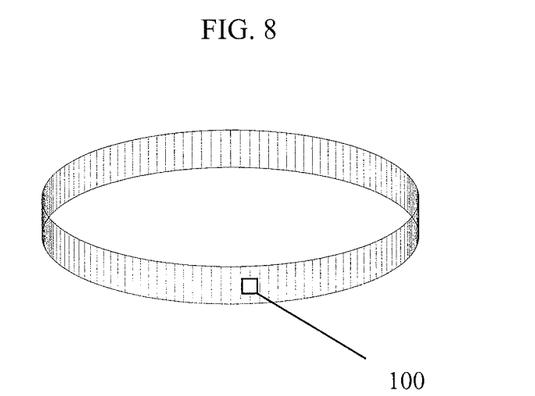
FIG. 8 depicts an article of wearing apparel having the sensor.

The sensor can be manufactured as part of a heart rate belt, or as a permanent part of, for example, underwear, sports apparel, a head band, or brassiere, in which case the textile material of these can act as such as the substrate of the sensor. FIG. 8 depicts the sensor 100 in a headband. It can be made to be extremely thin and dense, thanks to its construction, and can be washed without moisture penetrating to the internal parts of the sensor.

For placing on the skin, one of the layers of the layered structured described above can extend outside of the actual sensor area. When integrated in apparel, this layer is typically the substrate layer, but in a heart rate belt application, for example, the elastic belt or band to be stretched around the chest can be manufactured to also continue from some other layer of the structure. Generally, in such a construction there are at least three layers arranged permanently on top of each other, one of which forms the signal conductor layer and one continues as a textile-like or elastic structure, in such a way that it can be arranged around some part of the body, in order to bring the signalling surface of the electrode substantially against the skin. As described above, at least one and preferably two of the layers form in addition a moisture protection for the transmission conductor.

One particular embodiment that can be referred to is a heart rate belt application, in which the sensor structure described is combined with an elastic belt or band, which is made 'too long' at the factory, and from which part can be cut off, so that the reaming length of the band will be suitable for the user's body. A connector piece can be attached to the end of the band, which can be fitted to a counter piece connected to the sensor. The band can also be sewn or glued to form a unified loop, in which case no plastic components will be required. The individual fitting of the band can be made by the reseller, for example, in a sports-goods store. In particular, an individually fitted heart rate band makes it possible to avoid the use of plastic length-adjustment pieces, as these are typically thick relative to the actual belt or band, and can be unpleasant during exercise.

In addition, other conductors in addition to the electrode-signal transmission conductors can also be laminated in the sensor structure. Examples of these are antennae and other electrical/optical conductors relating to other electrical/optical functions integrated in the apparel/device totality in question.

With the aid of the sensor structure described, it is also possible to manufacture medical sensors, for example, for electroencephalography (EEG), or electrocardiography (ECG). There can then be tens, or even hundreds of measuring channels. Such sensors are made economical, durable, washable, and comfortable for the patient. Patients' fear of tests can also be reduced by the fact that the signal paths of the various channels can be integrated reliably and unnoticeably in a fabric construction, thus giving the measuring unit a pleasant appearance.

Figure 6:
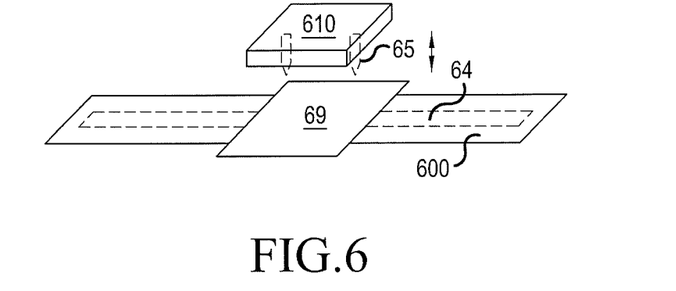
FIG. 6 shows the use of the sensor in connection with a detachable electronics and module.
Figure 7:
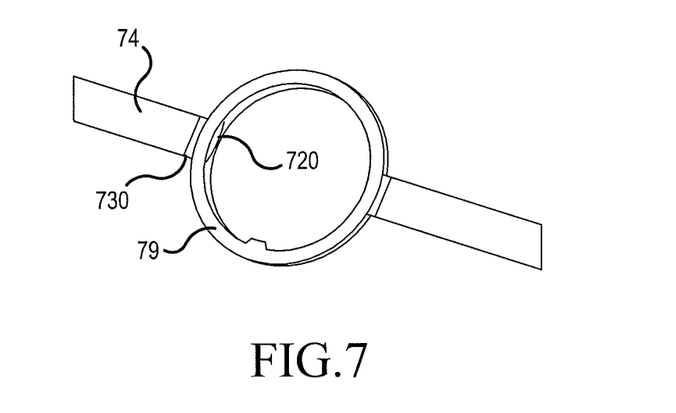
FIG. 7 shows in greater detail contacting according to one embodiment, with a detachable electronics module.

With reference to FIG. 6, the sensor can further comprise an installation zone 69 for attaching and detaching the electronics module 610, to which the signal transmission conductor 64 can be connected. In that case, the transmission conductor 64, disposed on substrate 600, is connected electrically to a contact area located in the installation zone 69. The installation zone shown in FIG. 7 can comprise, for example, the ring structure 79, in which metallic contact wires 720 are integrated. When the electronics module is detachably mounted in the installation zone 79, the contact wires 720 surround and make contact with the electronics module. FIG. 7 also shows one possible way to implement the joint 730 between the signal transmission conductor 74 and the contact wires 720. The joint 730 is preferably made using a joint moulding technique, which produces a durable joint with good electrical conductivity. The moulding technique can also be used as an aid in creating a durable joint 730 when using, for example, output conductive substances in the signal transmission conductor 64, 74. The electronics module can be advantageously installed to be able to be detached later. Typically the contact components in either the installation zone 69, 79 or in the electronic module are flexible when installing the module, to create a good contact. Such a sensor arrangement will also withstand machine washing. The electronics module 610 can also be connected to the transmission conductors 64 in other ways, for example, with the aid of press-studs 6s, as seen in FIG. 6, for example.

The electronics module typically contains means for transmitting, recording, or displaying a measured physiological signal. Typically it comprises a wireless signal transmitter, the terminal of which being, for example, a wristop computer, a computer, or some other heart-rate monitor.

What is claimed is:

1. An article of wearing apparel provided with a sensor for measuring a physiological signal from outside a body of a wearer of the apparel, comprising:
    a flexible substrate of the wearing apparel, which is permeable to moisture, said flexible substrate having a first end and a second end and a first surface and a second surface opposite to the first surface,
    at least one electrode of the sensor attached to said flexible substrate and having a signalling surface, said signalling surface extends through an opening in the flexible substrate to face in the same direction as the first surface of the flexible substrate,
    a signal transmission conductor connected electrically to said electrode,
    wherein an entire length of the signal transmission conductor is attached in a watertight manner to the second surface of the flexible substrate, said entire length of said signal transmission conductor being contained on said second surface of said flexible substrate without extending beyond the first end or the second end of said flexible substrate, and
    an installation zone, onto which an electronics module is attachable, is formed on the signal transmission conductor,
    wherein said signal transmission conductor is connected electrically to a contact area situated in the installation zone, so that when the electronics module is attached onto the installation zone, the contact area in the installation zone makes electrical contact with the electronics module.

2. The article of wearing apparel provided with the sensor according to claim 1, wherein the signal transmission conductor is attached to the substrate with the aid of at least one of a watertight and an electrically insulating layer, which is located between the signal transmission conductor and the substrate.

3. The article of wearing apparel provided with the sensor according to claim 2, wherein an intermediate layer is permanently attached to the substrate beneath the signal transmission conductor.

4. The article of wearing apparel provided with the sensor according to claim 3, wherein the intermediate layer is arranged to make the sensor unstretchable or poorly stretchable, however, while retaining its flexibility.

5. The article of wearing apparel provided with the sensor according to claim 3, wherein the signal transmission conductor is permanently attached to the intermediate layer.

6. The article of wearing apparel provided with the sensor according to claim 1, wherein the signal transmission conductor comprises a conductive substance spread in a fluid form selected from the group consisting of a conductive ink, a conductive polymer, and a coating with a metal-particle content.

7. The article of wearing apparel provided with the sensor according to claim 1, wherein the signal transmission conductor comprises a conductor applied in a solid form selected from the group consisting of a rubber, elastomer conductor, a metallic conductor, a conductive fibre, and a conductive textile.

8. The article of wearing apparel provided with the sensor according to claim 1, wherein the electrode is arranged on the substrate in such a way that there is a direct contact connection to its signalling surface from the side of the first surface of the substrate.

9. The article of wearing apparel provided with the sensor according to claim 1, wherein the electrode extends through the entire substrate in its thickness direction.

10. The sensor according to claim 1, wherein the electrode and the signal transmission conductor consist of a single layer or piece formed from essentially the same material.

11. The article of wearing apparel provided with the sensor according to claim 1, wherein the transmission conductor is located between two watertight layers attached to each other in a watertight manner.

12. The article of wearing apparel provided with the sensor according to claim 1, which comprises at least one conductor layer arranged under or on top of the signal transmission conductor, in such a way that an insulator laminate is arranged between the conductor layer and the signal transmission conductor.

13. The article of wearing apparel provided with the sensor according to claim 1, which further comprises at least one protective layer placed on top of the signal transmission conductor, so that the signal conductor remains in an inner layer of the sensor structure, in such a way that its elongation when the structure is bent is substantially less than that of the outer layers of the structure.

14. The article of wearing apparel provided with the sensor according to claim 1, wherein the substrate of the wearing apparel is of a textile material.

15. The article of wearing apparel provided with the sensor according to claim 1, wherein the contact area comprises a metallic conductor.

16. The article of wearing apparel provided with the sensor according to claim 1, wherein said electronics module contains means for transmitting, recording, or displaying a measured physiological signal.

17. The article of wearing apparel provided with the sensor according to claim 1, which comprises a layer structure, in which there are at least three layers arranged detachably on top of each other, one of which forms the signal transmission conductor and one continues as a textile or elastic structure, in such a way that it can be arranged around some part of the body, in order to bring the signalling surface of the electrode substantially against the skin.

18. The article of wearing apparel provided with the sensor according to claim 1, wherein the substrate continues in a unified form from the surface on the side of the signalling surface of the electrode to the second surface of the flexible substrate, in such a way that the signal transmission conductor remains essentially inside a tubular structure made from the substrate material.

19. The article of wearing apparel provided with the sensor according to claim 1, wherein the flexible substrate is a heart rate belt for positioning around a chest of the wearer of the apparel.

20. The article of wearing apparel provided with the sensor according to claim 1, wherein the flexible substrate is an innermost textile layer of the apparel.

21. The article of wearing apparel provided with the sensor according to claim 1, wherein said contact area comprises a press stud.

22. The article of wearing apparel provided with the sensor according to claim 1, wherein the flexible substrate extends over the whole area of the sensor, apart from the area of the electrode.

23. The article of wearing apparel provided with the sensor according to claim 1, wherein the flexible substrate is a sports brassiere for positioning around a chest of the wearer of the apparel.

24. The article of wearing apparel provided with the sensor according to claim 1, wherein the installation zone is configured for removable attachment of the electronics module.

25. The article of wearing apparel provided with the sensor according to claim 1, wherein the installation zone is configured for permanent attachment of the electronics module.

26. The article of wearing apparel provided with the sensor according to claim 1, wherein the sensor is waterproof, so that when the wearing apparel is washed, moisture is prevented from penetrating into the sensor.

27. The article of wearing apparel provided with the sensor according to claim 1, wherein the installation zone is circular in shape and has metallic contact wires integrated therein, so that when the electronics module is attached onto the installation zone, the metallic contact wires in the installation zone make electrical contact with the electronics module.

28. An article of wearing apparel provided with a sensor for measuring a physiological signal from outside a body of a wearer of the apparel, the sensor comprising:
  a flexible substrate of the wearing apparel, which is permeable to moisture, said flexible substrate having a first end and a second end and a first surface and a second surface opposite to the first surface,
  at least one electrode of the sensor attached to the flexible substrate and having a signalling surface, said signalling surface extends through an opening in the flexible substrate to face in the same direction as the first surface of the flexible substrate, and
  a signal transmission conductor, which is connected electrically to said electrode and attached in a watertight manner to the second surface of the flexible substrate, said signal transmission conductor being contained on said second surface of the flexible substrate without extending beyond the first end or the second end of the flexible substrate, and an installation zone, onto which an electronics module is attachable, is formed on the signal transmission conductor and a contact area is situated in the installation zone, wherein the signal transmission conductor is electrically connected to the contact area, so that when the electronics module is attached onto the installation zone, the contact area in the installation zone makes electrical contact with the electronics module.

29. The sensor according to claim 28, wherein said contact area comprises a metal conductor.

30. The article of wearing apparel provided with the sensor according to claim 28, wherein said electronics module contains means for transmitting, recording or displaying a measured physiological signal.

31. The article of wearing apparel provided with the sensor according to claim 28, wherein the flexible substrate extends over substantially an area of the sensor except for an area of the electrode.

32. The article of wearing apparel provided with the sensor according to claim 28, wherein the installation zone is circular in shape and has metallic contact wires integrated therein, so that when the electronics module is attached onto the installation zone, the metallic contact wires in the installation zone make electrical contact with the electronics module.

33. The article of wearing apparel provided with the sensor according to claim 28, wherein the substrate of the wearing apparel is of a textile material.

34. The article of wearing apparel provided with the sensor according to claim 28, wherein the flexible substrate is a heart rate belt for positioning around a chest of the wearer of the apparel.

35. A method for making an article of wearing apparel provided with the sensor for measuring a physiological signal from outside a body of a wearer of the apparel, the method comprising:

providing a flexible substrate of the wearing apparel, which is permeable to moisture, said flexible substrate having a first end and a second end and a first surface and a second surface opposite to the first surface, attaching at least one electrode of the sensor to said flexible substrate, the electrode having a signalling surface, said signaling surface extends through an opening in the flexible substrate to face in the same direction as the first surface of the flexible substrate, electrically connecting a signal transmission conductor to said electrode, an entire length of the signal transmission conductor being attached in a watertight manner to the second surface of the flexible substrate, said entire length of said signal transmission conductor being contained on said second surface of said flexible substrate without extending beyond the first end or the second end of said flexible substrate, and attaching an electronics module onto an installation zone formed on the signal transmission conductor, wherein said signal transmission conductor is connected electrically to a contact area situated in the installation zone, so that when the electronics module is attached onto the installation zone, the contact area in the installation zone makes electrical contact with the electronics module.

36. The method for making an article of wearing apparel provided with the sensor according to claim 35, further comprising:

removably attaching the electronics module onto the installation zone.

37. The method for making an article of wearing apparel provided with the sensor according to claim 35, further comprising:

permanently attaching the electronics module onto the installation zone.

* * * * *